United States Patent [19]

Leis, Jr. et al.

[11] Patent Number: 5,149,541
[45] Date of Patent: Sep. 22, 1992

[54] PSYLLIUM-CONTAINING PRODUCES WITH A DISTRIBUTION OF PARTICLE SIZE

[75] Inventors: Paul D. Leis, Jr., Hamilton; Larry E. Burns, Goshen; Karen R. Hafer, Cincinnati, all of Ohio

[73] Assignee: The Procter & Gamble Company, Cincinnati, Ohio

[21] Appl. No.: 657,619

[22] Filed: Feb. 20, 1991

Related U.S. Application Data

[63] Continuation of Ser. No. 252,848, Oct. 3, 1988, abandoned.

[51] Int. Cl.$^5$ .................. A61K 35/78; A61K 9/14; A61K 9/16; A61K 31/725
[52] U.S. Cl. .................... 424/489; 424/499; 424/439; 424/490; 424/493; 424/195.1; 514/892; 426/93; 426/598; 426/629
[58] Field of Search .............. 424/489, 439, 440, 52, 424/480, 195.1; 426/93

[56] References Cited

U.S. PATENT DOCUMENTS

| | | |
|---|---|---|
| 3,148,114 | 9/1964 | Fahrenbach et al. ............... 167/55 |
| 4,321,263 | 3/1982 | Powell et al. ...................... 424/195 |
| 4,344,931 | 8/1982 | Aguilar .............................. 424/52 |
| 4,459,280 | 7/1984 | Colliopoulos et al. ............. 424/35 |
| 4,511,561 | 4/1985 | Madaus et al. .................... 424/195.1 |
| 4,548,806 | 10/1985 | Colliopoulos et al. ........... 424/440 |
| 4,551,331 | 11/1985 | Rudin ............................... 424/195.1 |
| 4,565,702 | 1/1986 | Morley et al. .................... 426/93 |
| 4,639,367 | 1/1987 | Mackles ........................... 424/45 |
| 4,689,229 | 8/1987 | Banik ............................... 514/57 |
| 4,737,364 | 4/1988 | Kalogris ........................... 424/195.1 |
| 4,766,004 | 8/1988 | Moskowitz ........................ 426/658 |
| 4,797,286 | 1/1989 | Thakkar et al. .................... 424/456 |
| 4,812,315 | 3/1989 | Tarabishi .......................... 424/44 |
| 4,813,613 | 3/1989 | Salete .............................. 241/7 |
| 4,828,842 | 5/1989 | Furst et al. ...................... 424/480 |
| 4,847,092 | 7/1989 | Thakkar et al. .................... 424/456 |
| 4,849,222 | 7/1989 | Broaddus ......................... 514/23 |
| 4,911,889 | 3/1990 | Leland et al. .................... 422/26 |
| 4,978,529 | 12/1990 | Denick, Jr. ....................... 514/892 |
| 4,996,051 | 2/1991 | Meer et al. ....................... 514/892 |
| 4,999,200 | 3/1991 | Casillan ........................... 424/480 |
| 5,048,760 | 9/1991 | Barbera et al. .................... 241/9 |

FOREIGN PATENT DOCUMENTS 2616329 12/1988 France .

OTHER PUBLICATIONS

Anderson et al., Hypocholesterolemic Effects of Psyllium Mucilloid for Hypocholesterolemic Men, Federation Proceedings, 46 (3), p. 877 (1987).
Anderson et al., Dietary Fiber: Hyperlipidemia, Hypertension and Coronary Disease, American Journal of Gastroenteroogy, 81, pp. 907-919 (1986).
Fagerberg, The Effects of a Bulk Laxative (Metamuci®) on Fasting Blood Glucose Serum Lipids and Other Variables in Constipated Patients with Non-Insulin Dependent Adult Diabetes, Current Therapeutic Research, vol. 31 (2), pp. 166-172 (1982).
Gopani, "Isubgol Cultivation in India", Farm Bulletin, pp. 1-18 (1969; published by the Farm Information Unit, Directorate of Extension, Ministry of Food, Agriculture, Community Development and Cooperation, New Delhi, India).
Machado et al., Allergy, 34 (1), pp. 51-55 (1979).
Machado et al., Allergy, 38 (2), pp. 141-144 (1983).
Makarenko et al., Farm Zh, Jun., 1980, (3), pp. 77-78.
Physician's Desk Reference For Prescription Drugs, 9th Edition (1988); Medical Economics Company, Inc., pp. 642-644 (Metamucil®, sold by The Procter & Gamble Company).

Primary Examiner—Thurman K. Page
Assistant Examiner—E. J. Webman
Attorney, Agent, or Firm—Kim William Zerby; Douglas C. Mohl; Richard C. Witte

[57] ABSTRACT

Psyllium husk comprising particle sizes distributed such that: less than about 15% is larger than about 80 mesh, at least about 45% is within the range of from about 80 mesh to about 200 mesh, and less than about 40% is smaller than about 200 mesh. In addition, psyllium-containing products for oral administration comprising small particle size psyllium husk according to the present invention are described.

30 Claims, No Drawings

PSYLLIUM-CONTAINING PRODUCES WITH A DISTRIBUTION OF PARTICLE SIZE

This is a continuation of 252,848, filed Oct. 3, 1988, now abandoned.

BACKGROUND OF THE INVENTION

The present invention relates psyllium husk of a certain small particle size distribution; and to products containing such particle size psyllium husk suitable for oral administration, especially products to be mixed in liquids to form psyllium-containing drinks.

Products containing psyllium seed husk are known (e.g., Metamucil®, sold by the Procter & Gamble Company). Such products are useful for the benefits of normalizing bowel function and laxation. In addition, recent research has demonstrated the effectiveness of psyllium seed husk fiber in reducing human serum cholesterol levels, and in controlling blood glucose levels in diabetics. See, for example, J. W. Anderson, et al., *Fed. Proc.*, 46, 877 (1987); J. W. Anderson, et al., *Am. J. Gastroenterol.*, 81, 907-919 (1986); and S. Faberberg, *Curr. Ther. Res.*, 31, 166 (1982); all incorporated herein by reference in their entirety.

The palatability of psyllium-containing products vary depending on the form used, and, of course, the user's particular preference. Frequently, however, psyllium-containing products are viewed as having poor palatability. In particular, psyllium-containing products to be mixed with a liquid to form a drink are considered by many to be aesthetically objectionable for one or more of several reasons such as texture (e.g., grittiness, general mouth feel), viscosity, visual appearance, etc.

Therefore, improving the palatability of psyllium-containing products is a continuing need which would benefit a significant number of consumers. More palatable products may result in improved compliance for dosing regimens involving several doses or extended duration therapy. Thus, while psyllium can be (and in fact has been) combined with many carriers and flavorants in many forms, there continues to be a need for improved, highly palatable psyllium-containing products.

Current psyllium-containing products, such as products to be mixed with a liquid to form a drink, utilize subsequently more of larger particle size psyllium husk. It has been discovered by the present invention that by selecting a particular range of substantially smaller particle size psyllium, the aesthetics of psyllium-containing products are improved dramatically. In addition, in view of a large body of literature that states or intimates that reducing the particle size of other fiber materials (such as wheat bran) reduces the fiber's efficacy [e.g., See: Dietary Fiber in Health and Disease, pages 10-11 (Vahouny and Kritchevsky, editors; Plenum Press, New York, N.Y.; 1982); CRC Handbook of Dietary Fiber in Human Nutrition, pages 267-269 (Spiller, editor; CRC Press, Inc.; Boca Raton, Fla.; 1986); Handbook of Dietary Fiber, An Applied Approach, pages 152-153 (Dreher; Marcel Dekker, Inc., New York, N.Y.; 1987); Kirwan et al., *British Medical Journal*, 4, pages 187-189 (1974); Brodribb et al., *Gut*, 19, pages 60-63 (1978); and Cummings et al., *CMA Journal*, 123, pages 1109-1114 (1980)], the present invention is even more surprising since the psyllium of the present invention is essentially at least as efficacious as the substantially larger particle size psyllium used previously.

It is therefore an object of the present invention to provide psyllium husk and psyllium-containing products for oral administration having improved aesthetics. It is a further object to provide psyllium husk and psyllium-containing products to be mixed with a liquid to form a drink which are efficacious and have improved aesthetics, including texture, mouth feel, palatability, grittiness, and/or visual appearance.

These and other objects of the present invention will become readily apparent from the detailed description which follows.

All percentages and ratios used herein are by weight unless otherwise specified.

SUMMARY OF THE INVENTION

The present invention relates to psyllium husk comprising particle sizes distributed as follows: less than about 15% larger than about 80 mesh, at least about 45% within the range of form about 80 mesh to about 200 mesh, and less than about 40% smaller than about 200 mesh.

The present invention further relates to psyllium-containing products for oral administration comprising: (a) from about 1% to about 90% of psyllium husk having particle size distributions according to the present invention; and (b) from about 1% to about 99% carrier material suitable for oral administration to a human. Preferred are psyllium-containing products containing psyllium having at least 95% purity. Also preferred are psyllium-containing products in a form suitable for mixing with a liquid to form a drink, especially such products wherein the psyllium is agglomerated.

The present invention also relates to methods for providing laxation comprising orally administering to a human in need of laxation a safe and effective amount of psyllium having particle size distribution as described herein.

DETAILED DESCRIPTION OF THE INVENTION

1. Psyllium Husk of Limited Particle Size

The present invention relates to certain small particle size psyllium husk from psyllium seed, from plants of the Plantago genus. Various species such as *Plantago lanceolate, P. rugelii,* and *P. major* are known. Commercial psyllium husk include the French (black; *Plantago indica*), Spanish (*P. psyllium*) and Indian (blonde; *P. ovata*). Indian (blonde) psyllium husk is preferred for use herein. Also preferred is psyllium husk which is at least about 95% pure, more preferably more than about 95% pure, and most preferably at least about 97% pure.

Psyllium husk of the present invention comprises particle sizes distributed as follows: less than about 15% larger than about 80 mesh, at least about 45% within the range of from about 80 mesh to about 200 mesh, and less than about 40% smaller than about 200 mesh. Preferred are particle size distribution of: less than about 10% larger than about 80 mesh, at least about 65% within the range of from about 80 mesh to about 200 mesh, and less than about 25% smaller than about 200 mesh. More preferred are particle size distribution of: less than about 5% larger than about 80 mesh, at least about 75% within the range of from about 80 mesh to about 200 mesh, and less than about 20% smaller than about 200 mesh.

It is also preferred that the psyllium husk further comprise less than about 5% of particle sizes larger than about 60 mesh, and most preferably essentially no particle sizes larger than about 60 mesh. Also preferred is less than about 5% larger than about 80 mesh, and most preferred is essentially no particle sizes larger than about 80 mesh and less than about 25% larger than 100 mesh. Particle sizes and particle size distributions may be readily determined by one of ordinary skill in the art, for example by sieving using an Alpine Laboratory Air Jet Sieve, Type 200 LS (sold by Alpine American Corp., Natick Mass.).

The psyllium husk is obtained from the seed coat of psyllium seed. It is typical to remove the seed coat from the rest of the seed by, for example, slight mechanical pressure, and then to use only the seed coat. The seed coat is preferably removed and sanitized by methods known in the art (e.g., ethylene oxide) prior to reducing the particle size to that described herein. Methods for reducing psyllium particle size to those of the present invention are known in the art, or preferably may be reduced by the use of a stud mill (also known as "pin mills") under conditions which selectively reduce the psyllium husk size relative to non-husk impurity, thereby allowing for further purification if so desired.

2. Psyllium-containing Products

The present invention also relates to psyllium-containing products. These products comprise psyllium husk having particle sizes distributed according to the present invention, and one or more carrier materials suitable for oral administration to a human. Preferably, these products comprise from about 1% to about 99% psyllium husk, and from about 1% to about 99% carrier material; and more preferably from about 10% to about 98% psyllium husk and from about 2% to about 90% carrier material.

The carrier materials useful for the products of the present invention must be safe for oral administration to humans, and may be chosen by one of ordinary skill in the art as appropriate for the form and use intended for the product. Psyllium-containing product forms, methods for making, and carrier materials useful for these products, are described more fully, for example, in U.S. Pat. No. 4,459,280, to Colliopoulos et al., issued Jul. 10, 1984; U.S. Pat. No. 4,548,806, to Colliopoulos et al., issued Oct. 22, 1985; and U.S. Pat. No. 4,321,263, to Powell et all, issued Mar. 23, 1982; all of which are incorporated by reference herein in their entirety.

Most preferred are products of the present invention in dry powder form suitable for mixing in a liquid (typically water) to form a psyllium-containing drink. Preferred carrier materials for such powder forms are known and are described in detail, for example, in U.S. Pat. Nos. 4,459,280 and 4,548,806, incorporated hereinbefore by reference. Preferred are such powders (preferably sugar free) comprising maltodextrin. Also especially preferred are powders comprising agglomerates of psyllium and/or coated psyllium, especially agglomerated with maltodextrin and/or sucrose.

Psyllium-containing powders suitable for mixing in a liquid comprising from about 10% to about 98% of psyllium husk having particle sizes distributed according to the present invention (more preferably from about 20% to about 95% psyllium husk), and from about 0% to about 60% maltodextrin (more preferably from about 2% to about 50% maltodextrin) are preferred. Psyllium-containing products according to the present invention containing sugar (e.g., sucrose) comprise from about 10% to about 60% (preferably from about 20% to about 55%) psyllium husk, from about 35% to about 90% sugar, and from about 0% to about 5% maltodextrin. Sugar free products typically comprise from about 40% to about 98% (preferably from about 50% to about 95%) of psyllium husk according to the present invention, and from about 1% to about 60% (preferably from about 2% to about 50%) of maltodextrin. Preferred compositions comprise agglomerated psyllium, and also preferred are compositions wherein the carrier material comprises citric acid.

3. Methods for Providing Laxation

The present invention also relates to methods for providing laxation to a human in need of such treatment. These methods comprise administering to a human in need of such treatment a safe and effective amount of psyllium having particle sizes distributed according to the present invention, preferably in a psyllium-containing product of the present invention (e.g., a psyllium-containing drink).

Ingestion of from about 1 gram to about 30 grams per day of the psyllium husk according to the present invention is appropriate in most circumstances to produce laxation. However, this can vary with the size and condition of the patient, and such matters will, of course, be up to the attending physician. However, since the psyllium material is non-toxic, even higher ingestion levels can be used without undue side effects. A typical dose for laxation purposes involves administering from about 2.5 to about 15 grams of psyllium husk in one dose.

The following examples further describe and demonstrate embodiments within the scope of the present invention. These examples are given solely for the purpose of illustration and are not to be construed as limitations of the present invention, as many variations thereof are possible without departing from the spirit and scope.

EXAMPLE 1

Raw blond psyllium husk [95% purity; ethylene oxide sanitized; particle size distribution approximately: on 20 mesh (841 microns)=4.6%, thru 20 on 40 mesh (420 microns)=62.6%, thru 40 on 60 mesh (250 microns)=23.1%, thru 60 on 100 mesh (149 microns)=7.2%, thru 100 on 140 mesh (105 microns)=1.4%, thru 140 on 200 mesh (74 microns)=0.7%, thru 200 mesh (<74 microns) =0.4%] is selectively comminuted by using an Alpine Pin Mill (Model No. 160 UPZ; flow rate=70 kg/hr; full pin density; 18,000 rpms; sold by Alpine American Corp., Natick, Mass.) to maximize the through 80 mesh on 200 mesh fraction. The comminuted psyllium husk obtained has approximately the following particle size distribution: on 80 mesh (>177 microns)=15%; thru 80 on 100 mesh (177-149 microns)=2.5%; thru 100 on 120 mesh (149-125 microns)=14.2%; thru 120 on 140 mesh (125-105 microns)=14.9%; thru 140 on 170 mesh (105-95 microns)=17.7%; thru 170 on 200 mesh (95-74 microns)=16.0%; thru 200 on 325 mesh (74-44 microns) =11.2%; and thru 325 mesh (<44 microns)=8.5%.

The selectively comminuted psyllium husk is purified by sifting over a 60 mesh screen to sieve out much of the dark material, and then sieved to collect thru 80 on 200 mesh particle size psyllium husk according to the present invention. This psyllium is then used to prepare the following sugared product prepared by dry mixing the ingredients in a Hobart mixer (Model No. N-50).

| Ingredient | Percent of Formula |
| --- | --- |
| Sucrose | 63.43 |
| Citric Acid | 2.54 |
| Orange Flavor | 1.59 |
| Psyllium | 32.35 |
| FD&C Yellow No. 6 | 0.10 |

One tablespoon of this product is dispersed in 8 oz. of water to produce a drink containing approximately 5.1 grams of psyllium. Consumption of this drink by a human is effective for providing laxation benefits.

EXAMPLE 2

Utilizing psyllium husk milled as described in Example 1 collected thru 80 mesh, the following sugar free product is prepared.

| Ingredient | Percent of Formula |
| --- | --- |
| Psyllium | 75.80 |
| Maltrin | 5.50 |
| Citric Acid | 11.50 |
| Potassium Citrate | 1.14 |
| Aspartame | 1.16 |
| Flavor | 4.80 |
| FD&C Yellow No. 5 | 0.067 |
| FD&C Yellow No. 6 | 0.048 |

The composition is prepared by dry mixing the ingredients less approximately 3% of the maltrin, and then agglomerating with the remainder of the maltrin (aqueous solution) in a top spray, fluid bed agglomerater. One teaspoon of this product is dispersed in 8 ounces of water to product a drink containing approximately 3.4 grams of psyllium. Consumption of this drink by a human is effective for providing laxation benefits.

What is claimed:

1. Psyllium husk comprising particle sizes distributed as follows: less than about 5% larger than about 60 mesh, less than about 15% larger than about 80 mesh, at least about 45% within the range of from about 80 mesh to about 200 mesh, and less than about 40% smaller than about 200 mesh.

2. A method for providing laxatin to a human comprising administering to a human in need of such treatment a safe and effective amount for laxation of psyllium husk having particle sizes distributed according to claim 1.

3. Psyllium husk according to claim 1 comprising less than about 5% of particle sizes larger than about 80 mesh.

4. A method for providing laxation to a human comprising administering to a human in need of such treatment a safe and effective amount for laxation of psyllium husk having particle sizes distributed according to claim 3.

5. A psyllium-containing drink mix composition comprising:
   (a) from about 10% to about 99% psyllium husk having a particle size distribution according to claim 1;
   (b) from about 1% to about 90% of carrier material selected from the group consisting of sugar, maltodextrin, citric acid, flavoring agents, coloring agents, and combinations thereof;
and wherein further said composition is in a form dispersible in an aqueous liquid.

6. A psyllium-containing drink mix composition according to claim 5 comprising from about 1% to about 60% maltodextrin.

7. A psyllium-containing drink mix composition according to claim 6 comprising maltodextrin coated psyllium husk.

8. A psyllium-containing drink mix composition according to claim 5 comprising from about 35% to about 90% sugar.

9. A psyllium-containing product for oral administration comprising:
   (a) from about 1% to about 99% of psyllium husks having particle size distribution of less than about 5% larger than about 60 mesh, less than about 15% larger than about 80 mesh, at least about 45% within the range of from about 80 mesh to about 200 mesh, and less than about 40% smaller than about 200 mesh; and
   (b) from about 1% to about 99% carrier materials suitable for oral administration to a human.

10. The psyllium-containing product according to claim 9 when the psyllium husk is at least about 95% pure.

11. The psyllium-containing product according to claim 9 wherein the particle size distribution of the psyllium comprises no particles larger than about 80 mesh.

12. The psyllium-containing product according to claim 11 wherein the psyllium husk is at least about 95% pure.

13. The psyllium-containing product according to claim 9 in a powder form wherein the carrier materials are selected from the group consisting of drink mix carrier materials.

14. The psyllium-containing product according to claim 13 comprising coated psyllium.

15. A method for providing laxation to a human comprising administering to a human in need of such treatment a safe and effective amount for laxation of a psyllium-containing product according to claim 14.

16. The psyllium-containing product according to claim 13 wherein the carrier materials comprise material selected from the group consisting of sucrose, maltodextrin, citric acid, and combinations thereof.

17. A method for providing laxation to a human comprising administering to a human in need of such treatment a safe and effective amount for laxation of a psyllium-containing product according to claim 9.

18. A psyllium-containing drink mix product comprising:
   (a) from about 10% to about 60% psyllium husk having particle size distribution of less than about 5% larger than about 60 mesh, less than about 15% larger than about 80 mesh, at least about 45% within the range of from about 80 mesh to about 200 mesh, and less than about 40% smaller than about 200 mesh;
   (b) from about 35% to about 90% sugar; and
   (c) from about 0% to about 5% maltodextrin.

19. The psyllium-containing product according to claim 18 wherein the psyllium is agglomerated with materials which provide for dispersion of the psyllium husk in an aqueous liquid.

20. A psyllium-containing drink mix product comprising:
   (a) from about 40% to about 98% psyllium husk having particle size distribution of less than about 5% larger than about 60 mesh, less than about 15% larger than about 80 mesh, at least about 45% within the range of form about 80 mesh to about 200 mesh, and less than about 40% smaller than about 200 mesh; and (b) from about 1% to about 60% of maltodextrin.

21. The psyllium-containing product according to claim 20 wherein the psyllium is agglomerated with materials which provide for dispersion of the psyllium husk in an aqueous liquid.

22. Psyllium husk comprising particle sizes distributed as follows: no particles larger than about 80 mesh; at least about 45% within the range of from about 80 mesh to about 200 mesh; and less than about 40% smaller than about 200 mesh.

23. A method for providing laxation to a human comprising administering to a human in need of such treatment a safe and effective amount for laxation of psyllium husk having particle sizes distributed according to claim 22.

24. A psyllium-containing drink mix product comprising:

(a) from about 10% to about 98% of psyllium husk having particle size distribution of no particles no larger than about 80 mesh, at least about 45% within the range of from about 80 mesh to about 200 mesh, and less than about 40% smaller than about 200 mesh; and (b) from about 2% to about 90% carrier materials suitable for oral administration to a human, and wherein further said carrier materials comprise materials selected from the group consisting of sugar, maltodextrin, citric acid, aspartame, flavoring agent, coloring agent, and combinations thereof.

25. The psyllium-containing drink mix product according to claim 24 comprising from about 10% to about 60% psyllium husk and from about 35% to about 90% sugar.

26. A method for providing laxation to a human comprising administering to a human in need of such treatment a safe and effective amount for laxation of an aqueous dispersion of a psyllium-containing product according to claim 25.

27. The psyllium-containing drink mix product according to claim 24 comprising from about 40% to about 98% psyllium husk and from about 1% to about 60% of maltodextrin.

28. A method for providing laxation to a human comprising administering to a human in need of such treatment a safe and effective amount for laxation of an aqueous dispersion of a psyllium-containing product according to claim 27.

29. A method for providing laxation to a human comprising administering to a human in need of such treatment a safe and effective amount for laxation, of an aqueous dispersion of psyllium-containing product according to claim 24.

30. An aqueous liquid dispersion of psyllium husk comprising psyllium husks having a particle size distribution according to claim 22.

* * * * *

UNITED STATES PATENT OFFICE
CERTIFICATE OF CORRECTION

PATENT NO. : 5,149,541

DATED : September 22, 1992

INVENTOR(S) : Paul D. Leis, Jr., Larry E. Burns and Karen R. Hafer

It is certified that error appears in the above-identified patent and that said Letters Patent is hereby corrected as shown below:

Title page, item [54] and column 1, line 2, "Psyllium-Containing Produces With a Distribution of Particle Size" should be --Psyllium-Containing Products With a Distrubution of Particle Size--.

Column 1, line 1 "Produces" should be --Products--.

Column 2, line 19 "form" should be --from--.

Column 2, line 41 "1. Psyllium Husk of Limited Particle Size" should be --1. Psyllium Husk of Limited Small Particle Size--.

Column 5, line 46 "laxatin" should be --laxation--.

Signed and Sealed this

Twelfth Day of October, 1993

Attest:

BRUCE LEHMAN

Attesting Officer

Commissioner of Patents and Trademarks